United States Patent
Misawa

(10) Patent No.: US 10,471,173 B2
(45) Date of Patent: Nov. 12, 2019

(54) CONFORMABLE COMPOSITION FOR SKIN APPLICATIONS

(71) Applicant: ALCARE CO., LTD., Tokyo (JP)

(72) Inventor: Toshihide Misawa, Tokyo (JP)

(73) Assignee: ALCARE CO., LTD., Tokyo (JP)

( * ) Notice: Subject to any disclaimer, the term of this patent is extended or adjusted under 35 U.S.C. 154(b) by 0 days.

(21) Appl. No.: 15/502,722

(22) PCT Filed: May 20, 2015

(86) PCT No.: PCT/JP2015/064545
§ 371 (c)(1),
(2) Date: Feb. 8, 2017

(87) PCT Pub. No.: WO2016/021271
PCT Pub. Date: Nov. 2, 2016

(65) Prior Publication Data
US 2017/0232136 A1    Aug. 17, 2017

(30) Foreign Application Priority Data

Aug. 8, 2014   (JP) ................................. 2014-172053

(51) Int. Cl.
*A61L 24/04*   (2006.01)
*A61L 24/02*   (2006.01)
(Continued)

(52) U.S. Cl.
CPC ............. *A61L 24/043* (2013.01); *A61L 24/02* (2013.01); *A61L 24/046* (2013.01); *A61L 24/06* (2013.01); *A61L 24/08* (2013.01)

(58) Field of Classification Search
USPC .................................................. 523/111, 105
See application file for complete search history.

(56) References Cited

U.S. PATENT DOCUMENTS 4,477,325 A     10/1984   Osburn
4,496,357 A *   1/1985   Osburn ............... A61L 28/0003
                                                              516/103
(Continued)

FOREIGN PATENT DOCUMENTS

JP    08-000722 A    10/1984
JP    60-20976 A     2/1985
(Continued)

OTHER PUBLICATIONS

International Search Report issued for corresponding PCT/JP2015/064545 application.

(Continued)

*Primary Examiner* — Tae H Yoon
(74) *Attorney, Agent, or Firm* — IP Business Solutions, LLC

(57) ABSTRACT

Provided is a conformable composition for skin application having good formability into a predetermined shape, good conformability to skin, and shape retention after the contact with water such as excretion without loss of its shape. The conformable composition for skin application includes a reinforcing component, a rubber adhesive component, and a hydrophilic polymer compound, or the conformable composition for skin application at least includes 1 to 20 wt % a reinforcing component, 40 to 90 wt % a rubber adhesive component, and 2 to 40 wt % a hydrophilic polymer compound.

12 Claims, 2 Drawing Sheets

(51) Int. Cl.
*A61L 24/06* (2006.01)
*A61L 24/08* (2006.01)
*C08L 15/02* (2006.01)

(56) References Cited

U.S. PATENT DOCUMENTS

| | | | |
|---|---|---|---|
| 4,551,490 A | 11/1985 | Doyle et al. | |
| 5,492,943 A | 2/1996 | Stempel | |
| 6,451,883 B1 * | 9/2002 | Chen | A61F 5/443 524/31 |
| 2001/0031819 A1 * | 10/2001 | Iwata | C08G 18/62 524/443 |
| 2006/0141016 A1 * | 6/2006 | Sambasivam | A61K 36/81 424/445 |
| 2006/0188558 A1 * | 8/2006 | Jackson | A61K 9/7053 424/449 |
| 2011/0130698 A1 | 6/2011 | Kutsukake et al. | |

FOREIGN PATENT DOCUMENTS

| | | |
|---|---|---|
| JP | 05-200106 A | 8/1993 |
| JP | 10-314203 A | 12/1998 |
| JP | 2004-305725 A | 11/2004 |
| JP | 2006-181364 A | 7/2006 |
| JP | 2006-263042 A | 10/2006 |
| JP | 2009-273674 A | 11/2009 |
| JP | 2010-024225 A | 2/2010 |
| JP | 2011-127039 A | 6/2011 |
| WO | 99/11302 A1 | 3/1999 |
| WO | 2009/087877 A1 | 7/2009 |

OTHER PUBLICATIONS

Extended European Search Report mailed by the European Patent Office dated Mar. 23, 2018 in the corresponding European patent application No. 15830202.6-1109.

* cited by examiner

[Fig.1]
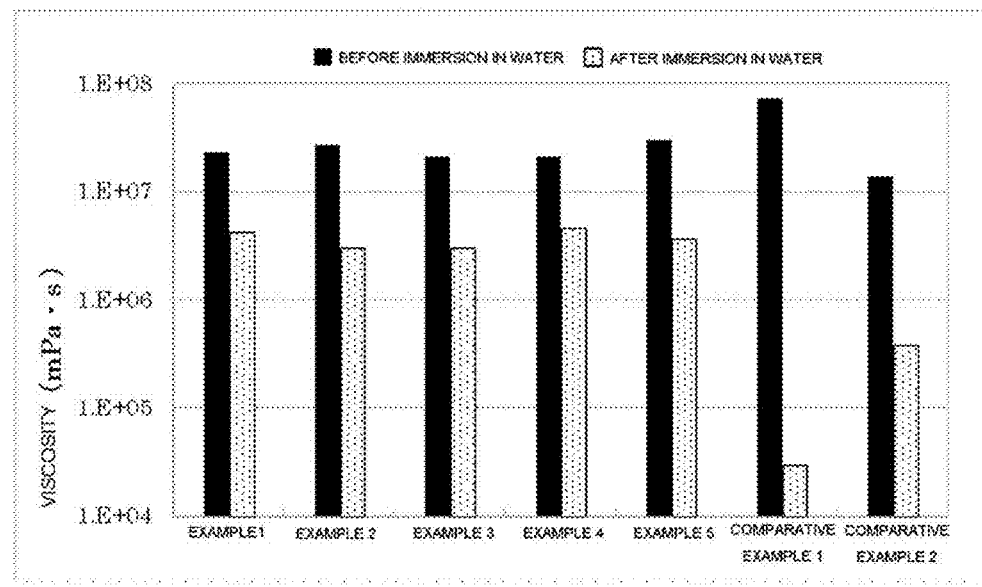
[Fig.2]
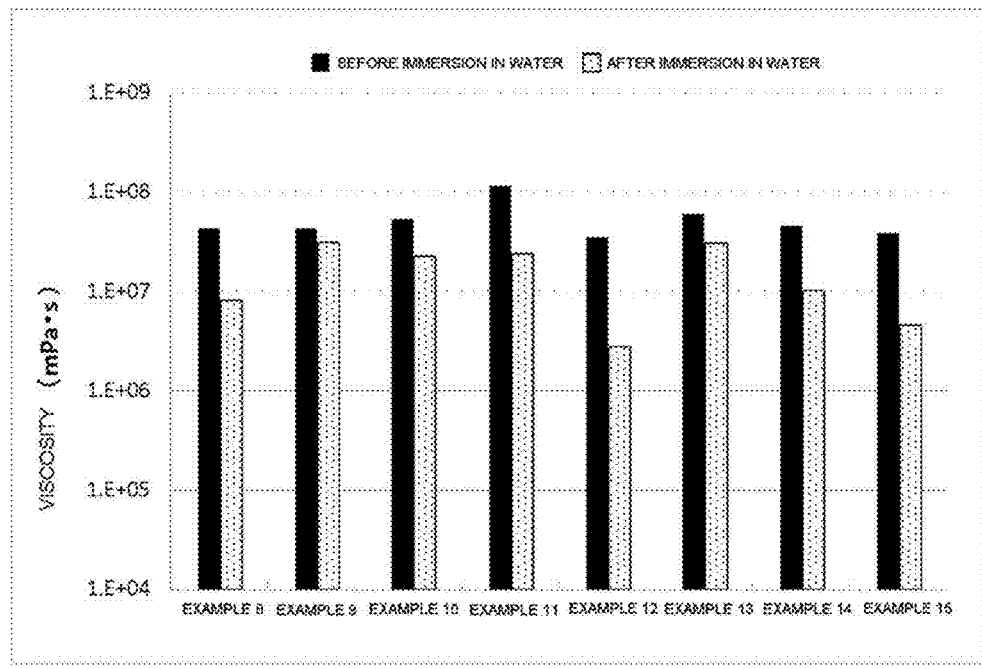

[Fig. 3]
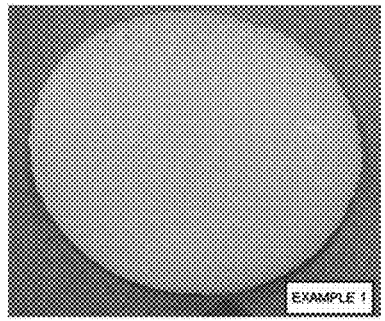
[Fig. 4]
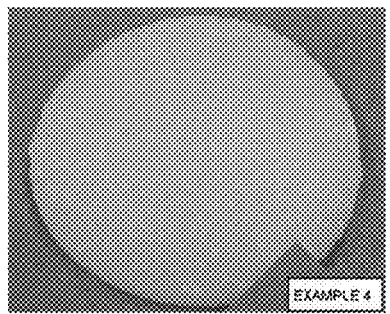
[Fig. 5]
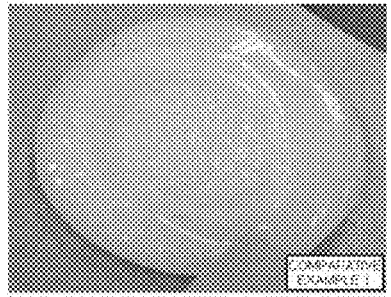
[Fig. 6]
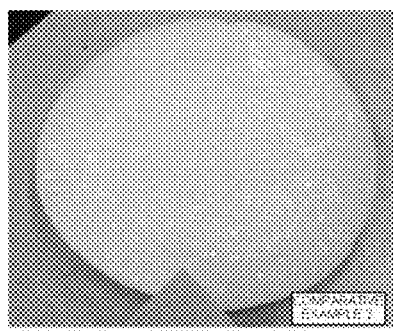

CONFORMABLE COMPOSITION FOR SKIN APPLICATIONS

TECHNICAL FIELD

The present invention relates to a conformable composition for skin application to be used for, for example, skin or wounds.

More specifically, the invention relates to a conformable composition for skin application for filling in the irregularities of the skin around a stoma or the gap between an ostomy appliance and a skin surface.

BACKGROUND ART

For individuals that cannot voluntarily control the excretion of feces and urine or individuals suffering from diseases of organs of digestive or urinary systems, openings, called stomata, are formed in the body surfaces by surgery to pull out the intestinal tracts or the urinary tracts until the body surfaces. In this case, an individual with a stoma (hereinafter, may be referred to as "stoma carrier") needs to wear an ostomy appliance, for temporarily retaining the excretion from the stoma, near the stoma. The ostomy appliance is composed of a pouch for receiving excretion and an adhesive sheet called face plate and is used by adhesively fixing the face plate to the periphery of the stoma.

The face plate of the ostomy appliance is generally made of a hydrocolloid skin-protecting material containing a hydrophilic polymer compound so that water from the skin and the excretion is absorbed even when being pasted to the skin for a long time.

Incidentally, some stoma carriers have wrinkles or irregularities in the skin around the stoma or have depression in the periphery of the stoma. In such a case, when the face plate of the ostomy appliance is pasted, the face plate cannot adhere to the skin in the periphery of the stoma, and a gap may be formed.

In addition, there may be a gap between the face plate and the skin due to, for example, flaps of the skin or bending of the body in use. Such a case has a problem of leakage of the excretion from the gap formed between the skin and the face plate to cause, for example, a bad smell or a skin disorder.

Accordingly, a skin-protecting composition in a paste form having adhesiveness has been developed in order to fill in the gap between the face plate of an ostomy appliance and the skin (see Patent Literature 1).

CITATION LIST

Patent Literature

Patent Literature 1: Japanese Unexamined Patent Application Publication No. 5-200106

The use of the adhesive paste composition can fill in the gap between the face plate of an ostomy appliance and the skin to prevent leakage of, for example, excretion. The composition for filling in the gap between the face plate of an ostomy appliance and the skin may be used in a variety of forms, such as paste and clay.

Incidentally, many stoma carriers are aged persons and become weak in the strength and dexterity of the hands. Accordingly, a composition in a clay form is desired to have softness to be readily formed into a predetermined shape and to be conformed to the skin.

At the same time, the composition filling in and adhering to the gap or irregularities of skin is required to have shape retention not to cause excessive deformation or loss of its shape or not to form a gap in the portion filled with the composition when the composition is brought into contact with water, such as excretion or perspiration from the stoma.

Although some of the commercially available adhesive compositions in clay forms, which are formed into predetermined shapes with bare hands to fill in the gaps or irregularities, have high shape retention and durability when they are pasted, they are hard to give poor formability into predetermined shapes and poor conformability to skin in use. Although some of the commercially available adhesive compositions have good formability and conformability to skin in use, they are sticky not to readily separate from fingers to show difficulty in handling with bare hands and have poor durability against water of excretion and readily deform to cause leakage.

SUMMARY OF INVENTION

Accordingly, it is an object of the present invention to provide a conformable composition for skin application that has a good formability into a predetermined shape and good conformability to skin, does not lose its shape even after the contact with water such as excretion, is less sticky during shaping with bare hands while maintaining appropriate adhesiveness, and has high shape retention.

The present invention provides a conformable composition for skin application comprising a reinforcing component, a rubber adhesive component, and a hydrophilic polymer compound.

The present invention also provides a conformable composition for skin application which can be formed into a predetermined shape with bare hands and is applied onto the skin around a stoma or to an ostomy appliance.

ADVANTAGEOUS EFFECTS

The present invention provides a conformable composition for skin application that has a good formability into a predetermined shape and good conformability to skin, does not lose its shape even after the contact with water such as excretion, has high shape retention, and has reduced stickiness. The conformable composition for skin application of the present invention can readily fill in the gap or irregularities of skin, has good adhesiveness and conformability not to cause leakage of, for example, excretion, and has high durability. The adhesive residue and irritation by peeling are low when the composition is removed or changed, and the physiological functions of the skin can be maintained or improved.

BRIEF DESCRIPTION OF DRAWINGS

FIG. 1 is a graph showing the viscometric results of the conformable compositions for skin application according to Examples 1 to 5 and Comparative Examples 1 and 2 before and after immersion in water.

FIG. 2 is a graph showing the viscometric results of the conformable compositions for skin application according to Examples 8 to 15 before and after immersion in water.

FIG. 3 is a photograph showing the result of a test for the shape retention of the conformable composition for skin application of Example 1 after immersion in physiological saline.

FIG. 4 is a photograph showing the result of a test for the shape retention of the conformable composition for skin application of Example 4 after immersion in physiological saline.

FIG. 5 is a photograph showing the result of a test for the shape retention of the conformable composition for skin application of Comparative Example 1 after immersion in physiological saline.

FIG. 6 is a photograph showing the result of a test for the shape retention of the conformable composition for skin application of Comparative Example 2 after immersion in physiological saline.

DESCRIPTION OF EMBODIMENTS

Preferred embodiments for implementing the present invention will now be described. The following embodiments are given for mere illustration of the present invention and should not be construed to limit the scope of the invention.

In an embodiment for implementing the present invention, the conformable composition for skin application comprises 1 to 20 wt % a reinforcing component, 40 to 90 wt % a rubber adhesive component, and 2 to 40 wt % a hydrophilic polymer compound.

In this embodiment, the content of the reinforcing component is preferably in a range of 1 to 15 wt %.

In this embodiment, the reinforcing component is preferably at least one thermoplastic elastomer selected from the group consisting of ethylene-(vinyl acetate) polymers, ethylene-(vinyl acetate) copolymers, acrylic resins, and hydrogenated styrene-butadiene rubber; the rubber adhesive component is preferably at least one selected from the group consisting of polyisobutylene, polyisoprene, polybutadiene, and butyl rubber; and the hydrophilic polymer is preferably at least one selected from the group consisting of sodium carboxymethyl cellulose, pectin, Karaya gum, and gelatin.

In the embodiment, the conformable composition preferably further includes a lipid composition. In such a case, the lipid composition preferably contains a surfactant.

In the embodiment, the lipid composition is preferably at least one selected from the group consisting of sphingolipids, sterols, glycerol fatty acid esters, and higher alcohols.

In the embodiment, the conformable composition preferably further comprises 0.3 to 30 wt % silica.

In the embodiment, the silica is preferably silylated silica.

In the embodiment, the conformable composition preferably further comprises modified silicone.

In the embodiment, the viscosity reduction rate defined by Expression (1) is preferably 95% at 2 hours after immersion in water:

[Expression 1]

$$\text{Viscosity reduction rate (\%)} = \{1 - (\text{viscosity of sample after immersion in water})/(\text{viscosity of sample before immersion in water})\} \times 100 \quad (1).$$

(Conformable Composition for Skin Application)

The conformable composition for skin application according to the embodiment comprises a reinforcing component, a rubber adhesive component, and a hydrophilic polymer compound and can be readily formed into a desired shape with bare hands. Specifically, the conformable composition for skin application is kneaded with the hands, is formed into a shape to adhere to the gap or irregularities of, for example, the skin around a stoma, and is used by making the composition for skin application adhere to the gap of the skin by the adhesiveness. Although the conformable composition for skin application according to the embodiment may be in a toroidal shape, like the faceplate for ordinary ostomy appliance, from the viewpoint of being arranged around a stoma in the use, the conformable composition may be in a stick or sheet shape for example. Furthermore, the composition can be in the form of paste if it contains some additive. In the following description, the conformable composition for skin application may be simply referred to "dermal composition", for convenience of explanation.

(Reinforcing Component)

The reinforcing component constituting the conformable dermal composition according to the embodiment may be of any type and can be, for example, selected from the following thermoplastic elastomers.

Examples of the thermoplastic elastomer used as the reinforcing component include styrene-butadiene rubber; styrene-isoprene-styrene (SIS) block copolymers; hydrogenated styrene-butadiene rubber (HSBR); styrene-butadiene-styrene (SBS) block copolymers; styrene-ethylene/propylene-styrene (SEPS) block copolymers; styrene-ethylene/butylene-styrene (SEBS) block copolymers; styrene-ethylene/ethylene/propylene-styrene (SEEPS) block copolymers; styrene-ethylene/butylene-olefin crystal (SEBC) block copolymers; olefin crystal-ethylene/butylene-olefin crystal (CEBC) block copolymers; chloroprene rubber; ethylene-(vinyl acetate) polymers; ethylene-(vinyl acetate) copolymers; acrylic resins, such as (meth)acrylate ester polymers and copolymers of (meth)acrylate esters; and acrylonitrile rubber. One or more of these thermoplastic elastomers can be selected without restriction.

In the conformable dermal composition according to the embodiment, among these thermoplastic elastomers, preferred are ethylene-(vinyl acetate) polymers; ethylene-(vinyl acetate) copolymers; acrylic resins, such as (meth)acrylate ester polymers and copolymers of (meth)acrylate esters; and hydrogenated styrene-butadiene rubber, and particularly preferred are ethylene-(vinyl acetate) polymers, ethylene-(vinyl acetate) copolymers, and hydrogenated styrene-butadiene rubber.

In the present specification, the term "(meth)acrylic acid" means both "acrylic acid" and "methacrylic acid".

The amount of the reinforcing component is usually 1 to 20 wt % and is preferably 1 to 15 wt %, more preferably 2 to 13 wt %, most preferably 3 to 10 wt %, based on the total weight of the conformable dermal composition.

The dermal composition containing the reinforcing component in an amount in the above-mentioned range can be formed into an appropriate shape by an appropriate force before application to skin, can have improved shape retention even after a predetermined time from the application to the skin, and does not lose its shape without adhesive residue when being peeled. In particular, an ethylene-(vinyl acetate) polymer or a combination of ethylene-(vinyl acetate) polymer and hydrogenated styrene-butadiene rubber improves the shape retention and the retention of the cohesive force when absorbing water. In this case, the conformable dermal composition preferably contains 3 to 16 wt % an ethylene-(vinyl acetate) polymer or ethylene-(vinyl acetate) polymer and 0.3 to 4 wt % hydrogenated styrene-butadiene rubber, more preferably 3.5 to 8 wt % an ethylene-(vinyl acetate) polymer or ethylene-(vinyl acetate) polymer and 0.3 to 1 wt % hydrogenated styrene-butadiene rubber, based on the total weight of the composition.

(Rubber Adhesive Component)

The rubber adhesive component constituting the conformable dermal composition according to the embodiment may be of any type and may be, for example, an adhesive containing a rubber component as a base polymer.

Examples of the rubber component used in the rubber adhesive component include polyisobutylene, polyisoprene, polybutadiene, butyl rubber, and silicone rubber. One or more of these rubber components can be selected without restriction.

In the conformable dermal composition according to the embodiment, among these rubber adhesive components, preferred are non-styrene rubber adhesive components, such as polyisobutylene, polyisoprene, polybutadiene, and butyl rubber; and particularly preferred is polyisobutylene.

The amount of the rubber adhesive component is preferably 40 to 90 wt %, more preferably 50 to 85 wt %, most preferably 55 to 80 wt %, based on the total weight of the conformable dermal composition.

The dermal composition containing the rubber adhesive component in an amount in the above-mentioned range has improved cohesiveness and shape retention and can be prevented from excessive swelling and flow, does not lose its shape after absorbing water, and can prevent adhesive residue when being peeled.

The adhesive strength and the softness of the dermal composition are improved, and thereby, for example, physical stimulation due to tightened skin or hardness of the dermal composition is alleviated.

(Hydrophilic Polymer Compound)

Examples of the usable hydrophilic polymer compound constituting the conformable dermal composition according to the embodiment include natural, semisynthetic, and synthetic hydrophilic polymer compounds.

Examples of the natural hydrophilic polymer compound include plant-derived polymers, such as gum Arabic, tragacanth rubber, galactan, guar gum, Locust been gum, Karaya gum, carrageenan, pectin, agar, and starch (for example, rice, corn, potato, and wheat starch); microorganism-derived polymers, such as xanthan gum, dextrin, dextran, succinoglucan, and pullulan; and animal-derived polymers, such as casein, albumin, and gelatin.

Examples of the semisynthetic hydrophilic polymer compound include starch polymers (e.g., carboxymethyl starch and methyl hydroxypropyl starch); cellulose polymers (e.g., methyl cellulose, ethyl cellulose, methyl hydroxypropyl cellulose, hydroxyethyl cellulose, cellulose sodium sulfate, hydroxypropyl cellulose, carboxymethyl cellulose, and sodium carboxymethyl cellulose); and arginate polymers (e.g., sodium arginate and propylene glycol arginate).

Examples of the synthetic hydrophilic polymer compound include vinyl polymers (e.g., poly(vinyl alcohol), poly(vinyl dimethyl ether), polyvinylpyrrolidone, and carboxyvinyl polymer); acrylic polymers (e.g., sodium polyacrylate and polyacrylamide); and polyethylene imines.

In the conformable dermal composition according to the embodiment, among these hydrophilic polymer compounds, preferred are sodium carboxymethyl cellulose, pectin, Karaya gum, and gelatin, and particularly preferred is sodium carboxymethyl cellulose.

In the conformable dermal composition according to the embodiment, these hydrophilic polymer compounds may be used alone or in combination.

The amount of the hydrophilic polymer compound is preferably 2 to 40 wt %, more preferably 4 to 20 wt %, most preferably 8 to 15 wt %, based on the total weight of the conformable dermal composition.

The dermal composition containing the hydrophilic polymer compound in an amount in the above-mentioned range well absorbs water of perspiration and excretion, reduces skin stimulation, such as skin maceration, and adheres to skin for a long time.

(Modified Silicone)

The conformable dermal composition according to the embodiment may contain a modified silicone as an optional component. The modified silicone may be anyone compatible with the rubber adhesive component and is preferably a liquid or has fluidity at ordinary temperature (15 to 25° C.).

Silicone can be modified with, for example, —O(EO)$_n$-group (polyether modification), —NH$_2$ group (amino modification), —OH group (hydroxyl modification), —CH$_2$OH group (carbinol modification), or —COOH group (carboxyl modification).

Among these modified silicones, particularly preferred in the embodiment is polyether-modified silicone having —O(EO)$_n$-group. The —O(EO)$_n$-group, which has a low chemical reactivity, in other words, is an inactive group, can stabilize the physiological properties of adhesives.

In the usable polyether-modified silicone, the main chain has, for example, a methicone, dimethicone, or polydimethylsiloxane backbone and a poly(ethylene glycol) side chain.

The modified silicone preferably has an HLB value of less than 7 and a viscosity of 700 to 3500 mm$^2$/s at 25° C.

The content of the modified silicone is preferably 0.05 to 50 wt %, more preferably 0.1 to 40 wt %, more preferably 0.3 to 30%, most preferably 0.5 to 10%, based on the total weight of the conformable dermal composition.

The dermal composition containing the modified silicone in an amount in the above-mentioned range can have improved formability with bare hands, shape retention after absorption of water, and releasability from fingers.

Herein, the term "releasability from fingers" indicates that the composition can be readily released or detached from fingers without remaining the adhesive component on the fingers when a dermal composition is formed with hands and does not cause sticky feeling of the fingers when the composition is removed after application to the skin for a predetermined time.

(Lipid Composition)

The conformable dermal composition according to the embodiment may contain a lipid composition as an optional component. The composition containing a lipid composition, such as a sphingolipid, a sterol, a glycerol fatty acid ester, and a higher alcohol, is expected to have a skin-protecting effect.

The lipid composition used in the embodiment preferably contains a sphingolipid and/or a sterol or contains at least one selected from the group consisting of sphingolipids, sterols, and surfactants and contains a higher alcohol. In such a case, the lipid composition preferably contains at least one surfactant selected from the group consisting of glycerol fatty acid esters, polyoxyalkylene alkyl ethers, polyoxyalkylene glycol fatty acid esters, and acylated lactic acid and/or its salts. In particular, the lipid composition preferably contains a glycerol fatty acid ester and acylated lactic acid and/or its salt as surfactants. This lipid composition preferably contains at least one selected from the group consisting of sphingolipids, sterols, glycerol fatty acid esters, and higher alcohols.

This lipid composition more preferably contains at least one selected from the group consisting of ceramides, cholesterols, polyglycerol fatty acid esters, and higher alcohols and preferably further contains acylated lactic acid and/or its salt.

In a preferred embodiment, the lipid composition further contains a ceramide and/or a cholesterol, a higher alcohol, a polyglycerol fatty acid ester, and acylated lactic acid and/or its salt.

In the lipid composition containing both a sphingolipid and a sterol, the total content of the sphingolipid and the sterol in the lipid composition is preferably 10 to 80 wt %, more preferably 20 to 80 wt %, and most preferably 30 to 70 wt %. In the lipid composition containing a sphingolipid or a sterol, the content of the sphingolipid or the sterol in the lipid composition is preferably 1 to 50 wt %, more preferably 2 to 30 wt %, and most preferably 5 to 20 wt %. These contents can also be applied to a case using a ceramide as a preferred sphingolipid and a cholesterol as a preferred sterol.

In the lipid composition containing a surfactant, the content of the surfactant in the lipid composition is preferably 10 to 60 wt %, more preferably 20 to 50 wt %, and most preferably 30 to 50 wt %.

In the lipid composition containing a higher alcohol, the content of the higher alcohol in the lipid composition is preferably 10 to 60 wt %, more preferably 20 to 50 wt %, and most preferably 30 to 50 wt %.

In the lipid composition containing a glycerol fatty acid ester as a surfactant, the content of the glycerol fatty acid ester in the lipid composition is preferably 10 to 50 wt %, more preferably 20 to 40 wt %, and most preferably 30 to 40 wt %.

In the lipid composition containing acylated lactic acid and/or its salt as a surfactant, the total content of the acylated lactic acid and its salt in the lipid composition is preferably 1 to 30 wt %, more preferably 2 to 30 wt %, and most preferably 5 to 20 wt %.

The lipid composition may preferably contain at least one selected from the group consisting of sphingolipids, sterols, and surfactants in a total amount of 5 to 80 wt % and one or more higher alcohols in a total amount of 10 to 50 wt %.

The lipid composition may more preferably contain at least one selected from the group consisting of sphingolipids, sterols, and glycerol fatty acid esters in a total amount of 5 to 80 wt % and one or more higher alcohols in a total amount of 10 to 50 wt %.

In the lipid composition containing a sphingolipid and/or a sterol, a higher alcohol, and a surfactant, the weight ratio, [sphingolipid and/or sterol]:[higher alcohol]:[surfactant], is preferably in a range of 1 to 5:2 to 5:3 to 5.

In the lipid composition containing a sphingolipid and/or a sterol, a higher alcohol, a glycerol fatty acid ester, and acylated lactic acid and/or its salt, the weight ratio, [sphingolipid and/or sterol] :[higher alcohol]:[glycerol fatty acid ester]:[acylated lactic acid and/or its salt], is preferably in a range of 1:4 to 5:3 to 4:1 to 2.

In the lipid composition containing a higher alcohol, a glycerol fatty acid ester, and acylated lactic acid and/or its salt, the contents thereof preferably decrease in this order, and the weight ratio, [higher alcohol]:[glycerol fatty acid ester] : [acylated lactic acid and/or its salt] is preferably in a range of 4 to 5:3 to 4:1 to 2.

(Sphingolipid and/or Sterol)

The sphingolipid and/or sterol that can be used in the lipid composition are lipids contained in horny intercellular lipids or analogs thereof. The ceramide, which is one of sphingolipids, is presumed to contribute to an improvement in the skin barrier function and have a high effect of supplementing horny intercellular lipids and is therefore conceivable to be a preferred component as a lipid composition according to the embodiment. In addition, the lipid composition containing such components has the potential of forming a lamellar structure.

The lamellar structure will now be described. The horny layer of the epidermis of skin is composed of horny cells, and a horny intercellular lipid exists between the horny cells. The horny intercellular lipid has a lamellar structure composed of water layers and oil (lipid) layers that are alternately disposed.

The conformable dermal composition according to the embodiment is formed of a lipid composition having the same structure as or a similar structure to that of the horny intercellular lipid, and may contain a specific lipid composition that can form a lamellar structure. Accordingly, application of such a conformable dermal composition to skin can enhance the skin-protecting effect or the moisturizing effect. Specifically, the lipid composition in the conformable dermal composition according to the embodiment is presumed to penetrate into the skin or remain on the skin surface, and this is presumed to contribute to provision of the moisturizing function and barrier function for the skin.

The sphingolipid to be used in the embodiment is preferably a ceramide or a glycosphingolipid composed of a ceramide and a saccharide linked to the ceramide. The term "ceramide" refers to a group of compounds of fatty acids amide-bonded to amino groups of, for example, sphingosine (2-amino-4-octadecene-1,3-diol), dihydrosphingosine (2-amimo-4-octadecane-1,3-diol), or phytosphingosine. The ceramide may be a natural ceramide, a pseudo ceramide, or a mixture thereof.

Since the ceramide is presumed to bear the moisturizing function of and the barrier function against the skin, it is preferable that the conformable dermal composition according to the embodiment contains a ceramide. The ceramide to be used may be a naturally derived product or a chemically synthetic product. In addition, the sphingoid base itself of the ceramide is presumed to have a skin-protecting effect.

The ceramide used in the dermal composition according to the embodiment can be any of types 1 to 6 (hereinafter, may be referred to such as "ceramides 1 to 6"), which are classified based on the structures of the hydrocarbon groups derived from the fatty acids bonded to the amino groups of sphingoid bases, such as sphingosine and sphinganine. In the conformable dermal composition according to the embodiment, one type of the ceramides may be used alone, or a combination of two or more types of the ceramides may be used.

In the dermal composition according to the embodiment, ceramide 2 is presumed to have a high effect of supplementing the horny intercellular lipid and is therefore preferably used.

Examples of the sterol used in the dermal composition according to the embodiment include cholesterol, dihydrocholesterol, lanosterol, dihydrolanosterol, desmosterol, stigmasterol, sitosterol, campesterol, brassicasterol, and ergosterol. Among these sterols, one or more sterols may be used, and cholesterol is preferred.

(Surfactant)

In the dermal composition according to the embodiment, the lipid composition preferably contains a surfactant for forming a lamellar structure. The surfactant may be any surfactant that can exhibit the effect of the dermal composition according to the embodiment, and an ionic surfactant (anionic surfactant, cationic surfactant, or ampholytic surfactant) or a nonionic surfactant can be appropriately used. The surfactant is more preferably a nonionic surfactant or an anionic surfactant and most preferably a nonionic surfactant.

(Anionic Surfactant)

Examples of the anionic surfactant include higher alkyl sulfuric acid ester salts, such as sodium lauryl sulfate and potassium lauryl sulfate; alkyl ether sulfuric acid ester salts, such as POE-triethanolamine lauryl sulfate and POE-sodium lauryl sulfate; alkylbenzene sulfonates, such as linear sodium dodecylbenzene sulfonate, linear triethanolamine dodecylbenzene sulfonate, and linear dodecylbenzene sulfonate; and acylated lactate salts, such as sodium lauroyl lactate, sodium stearoyl lactate, polyoxyethylene sorbitan fatty acid ester, polysorbate-60, and polysorbate-80. In the dermal composition according to the embodiment, the anionic surfactant is preferably acylated lactic acid and/or an acylated lactate salt. Herein, the term "POE" refers to polyoxyethylene and is also similarly used in the following explanation.

(Acylated Lactic Acid and/or Acylated Lactate Salt)

The lipid composition preferably contains acylated lactic acid and/or acylated lactate salt, i.e., one or both the acylated lactic acid and an acylated lactate salt.

The lipid composition containing acylated lactic acid and/or its salt is an emulsion lipid composition that can readily form a lamellar structure. From this viewpoint, acylated lactic acid and/or an acylated lactate salt is preferably used in a combination with a polyglycerol fatty acid ester described below.

The acyl group constituting the acylated lactic acid and/or acylated lactate salt may have a linear, branched, or cyclic chain. In detail, examples of the acyl group include an acetyl group, a propanoyl group, a butyryl group, a pivaloyl group, a valeryl group, a hexanoyl group, a stearoyl group, an isostearoyl group, a capryloyl group, a caprinoyl group, a lauroyl group, a myristoyl group, a palmitoyl group, a behenoyl group, an isopalmitoyl group, a linoloyl group, and an oleoyl group.

Preferred examples of the acyl group include a stearoyl group, an isostearoyl group, a capryloyl group, a caprinoyl group, a lauroyl group, a myristoyl group, a palmitoyl group, a behenoyl group, an isopalmitoyl group, a linoloyl group, and an oleoyl group. Among these acyl groups, a stearoyl group and an isostearoyl group are more preferred.

Preferred examples of acylated lactic acid include stearoyl lactic acid, isostearoyl lactic acid, caproyl lactic acid, behenoyl lactic acid, cocoyl lactic acid, lauroyl lactic acid, oleoyl lactic acid, 2-ethyl hexanoyl lactic acid, myristoyl lactic acid, palmitoyl lactic acid, 12-hydroxystearoyl lactic acid, and recinoleyl lactic acid. Among these acylated lactic acids, stearoyl lactic acid and isostearoyl lactic acid are more preferred.

Preferred examples of the acylated lactate salts include alkali metal salts, such as sodium salts and potassium salts; alkaline earth metal salts, such as calcium salts and magnesium salts; organic amine salts, such as ammonium salts, triethylamine salts, and triethanolamine salts; and basic amino acid salts, such as lysine and arginine. Among these salts, alkali metal salts are preferred, and sodium salt is more preferred.

These acylated lactic acids and/or acylated lactate salts may be used alone or in combination. The acylated lactic acid and/or acylated lactate salt used is more preferably sodium stearoyl lactate.

(Cationic Surfactant)

Examples of the cationic surfactant include alkyltrimethylammonium salts, such as stearyltrimethylammonium chloride and lauryltrimethylammonium chloride; and alkyldimethylbenzylammonium salts.

(Ampholytic Surfactant)

Examples of the ampholytic surfactant include betaine surfactants, such as 2-heptadecyl-N-carboxymethyl-N-hydroxyethylimidazolinium betaine, lauryl dimethyl aminoacetic acid betaine, alkyl betaine, amidobetaine, and sulfobetaine.

(Nonionic Surfactant)

Examples of the nonionic surfactant include glycerol fatty acid esters and their alkylene glycol adducts, polyglycerol fatty acid esters and their alkylene glycol adducts, propylene glycol fatty acid esters and their alkylene glycol adducts, pentaerythritol fatty acid esters (e.g., pentaerythrityl tetraisostearate), sorbitan fatty acid esters and their alkylene glycol adducts, fatty acid esters of sorbitol and their alkylene glycol adducts (e.g., sorbitan fatty acid esters, such as sorbitan monooleate, sorbitan monostearate, sorbitan monoisostearate, sorbitan monopalmitate, and sorbitan-monolaurate), poly(alkylene glycol) fatty acid esters, polyoxyalkylene alkyl ethers, glycerol alkyl ethers, polyoxyethylene alkylphenyl ethers, polyoxyalkylene modified silicone, polyoxyalkylene alkyl co-modified silicone, glycerol modified silicone, and polyoxyalkylene silicone co-modified silicone. In particular, preferred are glycerol fatty acid esters, sorbitan fatty acid esters and their alkylene glycol adducts, polyoxyalkylene alkyl ethers, and poly(alkylene glycol) fatty acid esters.

The nonionic surfactant may have any hydrophile-lipophile balance (HLB) value and ordinarily has an HLB value of 1 to 18, preferably 2 to 15, more preferably 2 to 10, and most preferably 2 to 8.

In the embodiment, as the HLB value of the nonionic surfactant, a known measured value may be used. For example, a measured value calculated by an emulsion method is used (see "Handobukku—Keshohin/Seizai Genryo—(Handbook of Cosmetics/Preparation Materials)", Nikko Chemicals Co., Ltd. (Feb. 1, 1977, revised version issued)). In actual measurement of the HLB value, a combination of sorbitan monostearate (e.g., NIKKOL SS-10 manufactured by Nikko Chemicals Co., Ltd., HLB value: 4.7) and polyoxyethylene sorbitan monostearate (e.g., NIKKOL TS-10 manufactured by Nikko Chemicals Co., Ltd., HLB value: 14.9) is used as reference surfactants; and liquid paraffin is used as a substance to be emulsified. If the liquid paraffin has a risk of a variation in HLB between different types or lots, the HLB value is measured at every time. The liquid paraffin emulsified with these two surfactants, the optimum ratio of the surfactants is determined, and the required HLB value of the liquid paraffin (HLB value for emulsification) is determined. The computation expression is shown in Expression 2:

[Expression 2]

$$\text{HLB value of liquid paraffin} = [\{(\text{HLB value of polyoxyethylene sorbitan monostearate}) \times (\text{used amount (mass \%)})\} + \{(\text{HLB value of sorbitan monostearate}) \times (\text{used amount (mass \%)})\}]/100$$

The required HLB value of liquid paraffin is usually about 10.1 to 10.3 although it varies depending on the type and the lot. The HLB value of a surfactant of interest is measured using the liquid paraffin of which the HLB value was determined. If the surfactant of interest is hydrophilic, sorbitan monostearate is used in combination with the surfactant. If the surfactant of interest is hydrophobic, polyoxyethylene sorbitan monostearate is used in combination with the surfactant. The liquid paraffin is emulsified to determine an optimum ratio showing a stable state, and the HLB value of the surfactant of interest is calculated from the expression.

(Glycerol Fatty Acid Ester)

The lipid composition preferably contains a nonionic surfactant, in particular, glycerol fatty acid ester of glycerol or polyglycerol having a degree of polymerization of 2 or more and fatty acid. The glycerol fatty acid ester contains both monoglycerol fatty acid ester and polyglycerol fatty acid ester.

The glycerol fatty acid ester may have a plurality of fatty acid moieties. Examples of the fatty acid include acetic acid, propionic acid, butyric acid, stearic acid, isostearic acid, lauric acid, myristic acid, oleic acid, caprylic acid, and capric acid. Among these fatty acids, stearic acid is preferred.

Examples of the monoglycerol fatty acid ester include glyceryl stearate, glyceryl isostearate, glyceryl laurate, glyceryl myristate, glyceryl oleate, glyceryl caprylate, and glyceryl caprate.

Examples of the polyglycerol fatty acid ester include polyglyceryl stearates, polyglyceryl isostearates, polyglyceryl laurates, polyglyceryl myristates, polyglyceryl oleates, polyglyceryl caprylates, and polyglyceryl caprates.

These glycerol fatty acid esters may be used alone or in combination. Among these glycerol fatty acid esters, polyglycerol fatty acid esters are preferred, and polyglyceryl stearates are more preferred.

Preferred examples of the polyglyceryl stearates include polyglyceryl-2, -4, -5, -6, and -10 monostearates, polyglyceryl-2, -3, -6, -9, and -10 distearates, polyglyceryl-4, -6, and -10 tristearates, and polyglyceryl-4, -6, and -10 pentastearates.

Preferred examples of polyglyceryl isostearates include polyglyceryl-2, -4, -6, and -10 monoisostearates, polyglyceryl-2, -3, -6, and -10 diisostearates, polyglyceryl-2 and -10 triisostearates, and polyglyceryl-2 tetraisostearate.

Preferred examples of polyglyceryl laurates include polyglyceryl-2, -3, -4, -5, -6, and -10 monolaurates and polyglyceryl-5 and -10 dilaurates.

Preferred examples of polyglyceryl myristates include polyglyceryl-5, -6, and -10 monomyristates, polyglyceryl-10 dimyristate, and polyglyceryl-5 trimyristate.

In the specific polyglycerol fatty acid esters mentioned above, the expression "polyglyceryl-n", such as polyglyceryl-2, -3, or -4, in the names of compounds represents the average number of monomer units (average degree of polymerization) of glycerol. For example, polyglyceryl-10 pentastearate means an ester compound (decaglycerol pentastearate) of a glycerol decamer (decaglycerol) and five molecules of stearic acid.

These polyglycerol fatty acid esters may be used alone or in combination.

The polyglycerol fatty acid ester used in the conformable dermal composition according to the embodiment is preferably decaglycerol fatty acid ester, more preferably polyglyceryl-4, -6, or -10 pentastearate, and most preferably polyglyceryl-10 pentastearate (decaglycerol pentastearate).

(Polyoxyalkylene Alkyl Ether)

The polyoxyalkylene alkyl ether used in the embodiment is a compound prepared by addition polymerization of a higher alcohol to an alkylene oxide.

The alkyl group of the polyoxyalkylene alkyl ether may be a linear or a branched. Examples of the alkyl group include octyl groups, nonyl groups, decyl groups, undecyl groups, dodecyl groups (lauryl groups), tridecyl groups, tetradecyl groups (myristyl groups), pentadecyl groups, hexadecyl groups (cetyl groups, palmityl groups), heptadecyl groups, octadecyl groups (stearyl groups), nonadecyl groups, icosyl groups, and behenyl groups (these alkyl groups include linear and branched groups).

The alkylene oxide moiety of the polyoxyalkylene alkyl ether maybe linear or branched. Examples of the alkylene oxide moiety include ethylene oxide, propylene oxide, butylene oxide, and —CH(CH$_3$)CH$_2$O—.

In the polyoxyalkylene alkyl ether used in the dermal composition according to the embodiment, one type of alkylene oxide may be copolymerized, or two or more types of alkylene oxides may be randomly copolymerized.

Preferred examples of the polyoxyalkylene alkyl ether used in the embodiment include POE(2) lauryl ether, POE (9) lauryl ether, POE(21) lauryl ether, POE(10) cetyl ether, POE(20) cetyl ether, POE(30) cetyl ether, POE(4) stearyl ether, and POE (20) stearyl ether. In particular, POE(9) lauryl ether and POE(4) stearyl ether are preferred.

(Poly(Alkylene Glycol) Fatty Acid Ester)

The poly(alkylene glycol) fatty acid ester used in the embodiment may be a known one that meets the effects of the dermal composition according to the embodiment and refers to an ester composed of a saturated or unsaturated fatty acid and poly(alkylene glycol). In this poly(alkylene glycol) fatty acid ester, the number of cycles of the polyalkylene group is preferably 8 to 100 and more preferably 10 to 80. Examples of the poly(alkylene glycol) fatty acid ester include poly (ethylene glycol) fatty acid esters, such as poly(ethylene glycol) monolaurate, poly(ethylene glycol) monostearate, and poly(ethylene glycol) monooleate; and propylene glycol fatty acid esters, such as propylene glycol monostearate, propylene glycol monolaurate, and propylene glycol monooleate. Among these poly(alkylene glycol) fatty acid esters, poly(ethylene glycol) monostearate (45E.O.) is preferred.

(Higher Alcohol)

The lipid composition preferably contains a higher alcohol. In the present disclosure, the term "higher alcohol" refers to an alcohol having 6 or more carbon atoms.

Any higher alcohol may be used, and preferred are aliphatic alcohols having 6 to 40 carbon atoms, more preferred are aliphatic alcohols having 8 to 36 carbon atoms, and most preferred are aliphatic alcohols having 10 to 24 carbon atoms. The aliphatic alcohol may be any aliphatic alcohol having a linear structure, a branched structure, or a cyclic structure and may be an unsaturated aliphatic alcohol having one or more double bonds or triple bonds or a saturated aliphatic alcohol.

Preferred examples of the higher alcohol include capryl alcohol, lauryl alcohol, myristyl alcohol, cetyl alcohol (cetanol), stearyl alcohol, oleyl alcohol, behenyl alcohol (1-docosanol), arachyl alcohol, 2-octyl lauryl alcohol, 2-hexyl decyl alcohol, isostearyl alcohol, and octyldodecanol. Among these higher alcohols maybe used alone or in combination.

Among these higher alcohols, preferred are oleyl alcohol, behenyl alcohol, and octyldodecanol; and particularly preferred is behenyl alcohol.

The conformable dermal composition may contain any amount of lipid composition, but the content of the lipid composition in the conformable dermal composition is preferably 0.1 wt % or more, more preferably 0.2 wt % or more, and most preferably 0.5 wt % or more, in order to obtain the effect of the lipid composition, and is preferably 20 wt % or less, more preferably 15 wt % or less, more preferably 10 wt % or less, and most preferably 6 wt % or less, from the viewpoints of providing appropriate adhesive strength and of manufacturing cost.

In the embodiment, the conformable dermal composition may be prepared by using a lipid composition preliminarily prepared by blending the components described above. Alternatively, the conformable dermal composition may be prepared by blending a reinforcing component, a rubber adhesive component, a hydrophilic polymer compound, individual components constituting a lipid composition, and any optional additive. Since the lipid composition readily forms a lamellar structure, it is preferable to prepare a lipid composition in advance by blending each of the components and then blending the lipid composition with other components, such as a resin, to form the conformable dermal composition.

(Other Additives)

The dermal composition according to the embodiment may further contain additives, such as a pH adjuster, a medicinal ingredient, a filler, a pigment, a plasticizer, and a tackifier, as optional components.

Any pH adjuster that meets the purpose of the dermal composition according to the embodiment may be used and can be selected from known pH adjusters without restriction. Examples of the pH adjuster include buffer solutions of citric acid, phosphoric acid, sodium hydrogen phosphate, anhydrous sodium hydrogen phosphate, pectin, anhydrous citric acid, alkali metal hydroxide, and organic acid.

Among these pH adjusters, preferred are buffer solutions of citric acid and anhydrous citric acid. The pH is preferably adjusted to a range of 4.0 to 6.0, which coincides with the pH of normal skin.

Any medicinal ingredient that meets the purpose of the dermal composition according to the embodiment may be used, and can be selected from known medicinal ingredients without restriction. Every possible medicines, such as physiologically active substances, antibacterial agents, anti-inflammatory analgesics, steroids, anesthetics, and antifungal agents, may be used.

Among these medicinal ingredients, physiologically active substances exhibiting local effects are preferred in order to maintain or improve the physiological functions (such as skin barrier function) of skin.

Examples of the physiologically active substance include urea, glycolic acid, amino acids (such as arginine, cysteine, glycine, lysine, proline, and serine) and derivatives thereof, protein hydrolysates (such as collagen, elastin, and keratin), mucopolysaccharides (such as hyaluronic acid, chondroitin sulfate, and heparin) and derivatives thereof, vitamin B group (such as thiamin, riboflavin, nicotinic acid, pyridoxine, pyridoxal, pyridoxamine, biotin, folic acid, and cyanocobalamin), ascorbic acid (vitamin C and derivatives thereof), retinoid (such as vitamin A, retinal, and retinoic acid), vitamin D (such as D2 and D3), vitamin E and derivatives thereof, carotenoids (such as carotene, lycopene, and xanthophyll), enzymes, coenzymes, and γ-oryzanol.

The filler may be powder or beads of silica or acrylic. In order to adjust the softness and the adhesiveness of the conformable dermal composition and to prevent bleeding from the modified silicone rubber adhesive composition or the reinforcing component, silica is preferred. In particular, silica having silanol groups blocked with inert functional groups (e.g., lower alkyl groups having 1 to 6 carbon atoms or a silyl group) is preferred from the viewpoint of shape retention when absorbing water and anti-bleeding of silicone, and silylated silica blocked with trialkyl silyl groups is more preferred.

The amount of silica to be blended is preferably 0.3 to 30 wt %, more preferably 0.5 to 15 wt %, most preferably 1 to 10 wt %, based on the total weight of the conformable dermal composition.

Any plasticizer that meets the purpose of the dermal composition of the embodiment can be used. Examples of the plasticizer include mineral oils, such as liquid paraffin and naphthenic oil; vegetable oils, such as olive oil, castor oil, and palm oil; animal oils, such as lanolin, turtle oil, and bees wax; and synthetic oils, such as silicone-based oil and ester-based oil. In particular, liquid paraffin is preferred.

Any known tackifier that meets the purpose of the dermal composition of the embodiment may be used. Examples of the tackifier include aliphatic copolymers; aromatic copolymers; aliphatic-aromatic copolymers; alicyclic copolymers; petroleum resins, such as alicyclic saturated hydrocarbon resins prepared by high-pressure hydrogenation of aromatic petroleum resins; rosin derivatives; terpene resins; coumarone-indene resins; and aliphatic hydrocarbon resins prepared by polymerization of aliphatic hydrocarbons such as 1,3-pentadiene. In particular, alicyclic saturated hydrocarbon resins are preferred.

The conformable dermal composition according to the embodiment preferably has a viscosity of $1 \times 10^6$ mPa·s or more before and after immersion in water for 2 hours. A viscosity within this range leads to enough shape retention even after absorption of water and low adhesive residue. In addition, the viscosity reduction rate of the viscosity of a specimen immersed in physiological saline (0.9% NaCl solution) and left to stand in a thermostat chamber of 37° C. for 2 hours compared to the viscosity before the immersion in the saline is preferably 95% or less, from the viewpoint of adhesive residue, more preferably 85% or less, and most preferably 75% or less. The lower limit of the viscosity reduction rate is preferably 0% or more, more preferably 5% or more, and most preferably 10% or more.

In particular, the viscosity reduction rate of the viscosity of a specimen immersed in physiological saline (0.9% NaCl solution) and left to stand in a thermostat chamber of 37° C. for 2 hours compared to the viscosity before the immersion in the saline is preferably 95% or less, from the viewpoint of adhesive residue, more preferably 85% or less, and most preferably 75% or less. The lower limit of the viscosity reduction rate of the viscosity of a specimen immersed in physiological saline (0.9% NaCl solution) and left to stand in a thermostat chamber of 37° C. for 2 hours compared to the viscosity before the immersion in the saline is preferably 0% or more, more preferably 5% or more, and most preferably 10% or more.

The values of viscoelasticity of the conformable dermal composition according to the embodiment measured in accordance with JIS K 7244 are preferably G' of 160000 Pa or less and G" of 135000 Pa or less. The dermal composition with viscoelasticity values within these ranges has softness, is readily handled with bare hands, and shows good followability to skin and also can maintain its shape after absorption of water without formation of a gap between the face plate and the skin.

The conformable composition for skin application of the embodiment can have the following aspects [1] to [14]:

[1] A conformable composition for skin application comprising a reinforcing component, a rubber adhesive component, and a hydrophilic polymer compound;

[2] A conformable composition for skin application comprising 1 to 20 wt % a reinforcing component, 40 to 90 wt % a rubber adhesive component, 2 to 40 wt % a hydrophilic polymer compound;

[3] The conformable composition for skin application according to aspect [1] or [2], wherein the reinforcing component is at least one selected from the group consisting of ethylene-(vinyl acetate) polymers, ethylene-(vinyl acetate) copolymers, acrylic resins, and hydrogenated styrene-butadiene rubber;

the rubber adhesive component is at least one selected from the group consisting of polyisobutylene, polyisoprene, polybutadiene, and butyl rubber; and the hydrophilic polymer compound is at least one selected from the group consisting of sodium carboxymethyl cellulose, pectin, Karaya gum, and gelatin;

[4] The conformable composition for skin application according to any one of aspects [1] to [3], further comprising a lipid composition;

[5] The conformable composition for skin application according to aspect [4], wherein the lipid composition contains a surfactant;

[6] The conformable composition for skin application according to aspect [4] or [5], wherein the lipid composition contains at least one selected from the group consisting of sphingolipids, sterols, glycerol fatty acid esters as surfactants and higher alcohols;

[7] The conformable composition for skin application according to aspect [4] or [5], wherein the lipid composition contains at least one selected from the group consisting of sphingolipids, sterols, and surfactants and contains a higher alcohol;

[8] The conformable composition for skin application according to aspect [4] or [5], wherein the surfactant is an anionic surfactant or a nonionic surfactant;

[9] The conformable composition for skin application according to aspect [7], wherein the lipid composition contains at least one selected from the group consisting of sphingolipids, sterols, and surfactants in a total amount of 5 to 80 wt % and contains one or more higher alcohols in a total amount of 10 to 50 wt %;

[10] The conformable composition for skin application according to any one of aspects [1] to [9], further comprising 0.3 to 30 wt % silica;

[11] The conformable composition for skin application according to aspect [10], wherein the silica is silylated silica;

[12] The conformable composition for skin application according to anyone of aspects [1] to [11], further comprising modified silicone;

[13] The conformable composition for skin application according to any one of aspects [1] to [12], having a viscosity reduction rate defined by Expression (1) is 95% or less at 2 hours after immersion in water; and

[14] The conformable composition for skin application according to any one of aspects [1] to [13], wherein the conformable dermal composition is applicable onto the skin around a stoma and/or to an ostomy appliance with bare hands.

Conformable dermal compositions were produced by the following process. Characteristics of the conformable dermal compositions were evaluated by the following procedures.

EXAMPLES

The conformable dermal compositions according to the embodiment will be described in more detail based on Examples, but should not be limited to the following Examples.

In Examples, lipid compositions A to E having formulations shown in Table 1 were used. In Table 1, ceramide 2 refers to TIC-001 manufactured by Takasago International Corporation.

TABLE 1

| Lipid composition (wt %) | | A | B | C | D | E |
|---|---|---|---|---|---|---|
| Sphingolipid | Ceramide 2 | 10 | — | 20 | 50 | 30 |
| Sterol | Cholesterol | — | — | — | — | — |
| Higher alcohol | 1-Docosanol | 45 | 50 | — | — | — |
| | Myristyl alcohol | — | — | — | 30 | — |
| | Octyldodecanol | — | — | 30 | — | 20 |
| Surfactant | Polyglyceryl-10 pentastearate | 34.2 | 38 | — | — | — |
| | Pentaerythrityl tetraisostearate | — | — | 50 | — | — |
| | Sorbitan monostearate | — | — | — | — | 50 |
| | Na stearoyl lactate | 10.8 | 12 | — | — | — |
| | POE(9) lauryl ether | — | — | — | 20 | — |

\* The mark "—" in the table indicates that the material is not compounded (the same applies the following tables).
\*\* The HLB values of the surfactants are as follows:
Polyglyceryl-10 pentastearate: 3.5
Pentaerythrityl tetraisostearate: 6.0
Sorbitan monostearate: 6.0
POE(9) lauryl ether: 14.5

Example 1

A reinforcing component (ethylene-(vinyl acetate) copolymer, manufactured by Tosoh Corporation, trade name "Ultrathene 760", 6.1 wt %), a rubber adhesive component (polyisobutylene, manufactured by JX Nippon Oil & Energy Corporation, trade name "Himol 6H", 65.7 wt %), and a modified silicone (polyether modified silicone, manufactured by Dow Corning Toray Co., Ltd., trade name "Emulsifier 10", 6.8 wt %) were charged in a pressurizing kneader and were sufficiently mixed under pressure into a uniform mixture. Subsequently, an additive (silica, manufactured by Nippon Aerosil Co., Ltd., trade name "Aerosil RX 300-5", 6.8 wt %), a hydrophilic polymer compound (sodium carboxymethyl cellulose, manufactured by Nippon Paper Chemicals Co., Ltd., 13.0 wt %), a lipid composition (lipid composition A, 1.0 wt %), and a pH adjuster (citric acid, manufactured by Showakako Co., Ltd., trade name "Citric Acid Anhydrous Powder", 0.6 wt %) were added to the mixture and were mixed into a uniform composition, followed by rolling to give a conformable dermal composition having a thickness of 1.5 mm.

Example 2

A conformable dermal composition of Example 2 was prepared as in Example 1 except that the content of polyisobutylene was changed to 66.6 wt % and the lipid composition A was replaced with 0.1 wt % ceramide 2.

Example 3

A conformable dermal composition of Example 3 was prepared as in Example 1 except that the content of polyisobutylene was changed to 66.6 wt % and the content of lipid composition A was changed to 0.1 wt %.

Example 4

A conformable dermal composition of Example 4 was prepared as in Example 1 except that the content of polyisobutylene was changed to 66.6 wt % and the lipid composition A was replaced with 0.1 wt % lipid composition B.

Example 5

A conformable dermal composition of Example 5 was prepared as in Example 1 except that the content of polyisobutylene was changed to 66.7 wt % and the lipid composition A was not blended.

Example 6

A conformable dermal composition of Example 6 was prepared as in Example 1 except that the content of ethylene-(vinyl acetate) copolymer was changed to 9.6 wt %, the content of polyisobutylene was changed to 65.6 wt %, the content of silylated silica was changed to 4.1 wt %, and lipid composition A was replaced with 0.3 wt % ceramide 2.

Example 7

A conformable dermal composition of Example 7 was prepared as in Example 1 except that the content of ethylene-(vinyl acetate) copolymer was changed to 4.8 wt %, the content of polyisobutylene was changed to 67.7 wt %, and lipid composition A was replaced with 0.3 wt % ceramide 2.

Example 8

An example containing a reinforcing component (hydrogenated styrene-butadiene rubber, manufactured by JSR Corporation, HSBR), a plasticizer (liquid paraffin, manufactured by Kaneda Co., Ltd., Hicall K-350), a tackifier (commercially available alicyclic saturated hydrocarbon resin, manufactured by Arakawa Chemical Industries, Ltd., Alcon P-100), a filler (silica), and a pH adjuster (citric acid) will be described.

In Example 8, hydrogenated styrene-butadiene rubber and liquid paraffin were charged in a pressurizing kneader and were sufficiently mixed into a uniform mixture.

Subsequently, an ethylene-(vinyl acetate) copolymer and polyisobutylene were added to the mixture and were mixed into a uniform mixture. A hydrophilic polymer compound (sodium carboxymethyl cellulose: CMC-Na), a filler (silica), a lipid composition (lipid composition A), and a pH adjuster (citric acid) were then added to the mixture, followed by mixing into a uniform composition to prepare a dermal composition of Example 8.

In Example 8, polyisobutylene (72.4 wt %), hydrogenated styrene-butadiene rubber (0.5 wt %), liquid paraffin (0.2 wt %), an ethylene-(vinyl acetate) copolymer (5.5 wt %), silica (6.8 wt %), sodium carboxymethyl cellulose (CMC-Na, 13.0 wt %), citric acid (0.6 wt %), and lipid composition A (1 wt %) were mixed and stirred to prepare the conformable dermal composition of Example 8.

Example 9

A conformable dermal composition of Example 9 was prepared as in Example 8 except that the content of polyisobutylene was changed to 58.7 wt % and a tackifier (13.7 wt %) was further blended in the composition.

Example 10

A conformable dermal adhesive of Example 10 was prepared as in Example 8 except that the content of hydrogenated styrene-butadiene rubber was changed to 3.4 wt %, the content of liquid paraffin was changed to 1.4 wt %, the content of the ethylene-(vinyl acetate) copolymer was changed to 4.8 wt %, and the content of polyisobutylene was changed to 69.0 wt %.

Example 11

A conformable dermal composition of Example 11 was prepared as in Example 8 except that the content of polyisobutylene was changed to 62.2 wt % and the content of the ethylene-(vinyl acetate) copolymer was changed to 15.7 wt %.

Example 12

A conformable dermal composition of Example 12 was prepared as in Example 9 except that lipid composition A was replaced with lipid composition C (1 wt %).

Example 13

A conformable dermal composition of Example 13 was prepared as in Example 9 except that lipid composition A was replaced with lipid composition D (1 wt %).

Example 14

A conformable dermal composition of Example 14 was prepared as in Example 9 except that lipid composition A was replaced with lipid composition E (1 wt %).

Example 15

In Example 15, a reinforcing component (ethylene-(vinyl acetate) copolymer, 6.1 wt %), a rubber adhesive component (polyisobutylene, manufactured by JX Nippon Oil & Energy Corporation, trade name "Himol 6H", 65.6 wt %), and modified silicone (polyether modified silicone, manufactured by Dow Corning Toray Co., Ltd., trade name "EMULSIFIER 10", 6.8 wt %) were charged in a pressurizing kneader and were sufficiently mixed under pressure into a uniform mixture. Subsequently, a filler (silylated silica, 6.9 wt %), a hydrophilic polymer compound (sodium carboxymethyl cellulose, manufactured by Nippon Paper Chemicals Co., Ltd., 13.0 wt %), a lipid composition (lipid composition A, 1.0 wt %), and a pH adjuster (citric acid, manufactured by Showakako Co., Ltd., trade name "Citric Acid Anhydrous Powder", 0.6 wt %) were added to the mixture and were mixed into a uniform composition, followed by rolling to give a conformable dermal composition having a thickness of 1.5 mm.

COMPARATIVE EXAMPLES

Comparative Examples 1 and 2

Instead of the conformable dermal compositions of the embodiment, commercially available conformable dermal compositions (Comparative Example 1: manufactured by Hollister, "Adapt (registered trademark) Skin Barrier Paste", Comparative Example 2: manufactured by Coloplast, "Moldable Ring"), were evaluated.

[Viscosity]

A specimen (about 2 g) was sampled from each of the conformable dermal compositions of Examples and Comparative Examples and was subjected to viscometry with a flow tester (manufactured by Shimadzu Corporation, Shimadzu Flow Tester CFT-500) at a temperature of 30° C., a preheating time of 180 sec, a dice diameter of 1 mm, a dice length of 5 mm, and an extrusion pressure of 100 kgf. This viscosity was recorded as an initial viscosity before immersion in water.

Another circular specimen having a diameter of 53 mm and a thickness of 1.5 mm was sampled from each composition and was immersed in physiological saline (0.9% NaCl solution) and was left to stand in a thermostat chamber of 37° C. for 2 hours. On this occasion, one of the circular surfaces of each specimen was provided with a water-repellent release sheet, and the specimen was then immersed in the saline. About two grams of the immersed specimen were sampled and were subjected to viscometry as in the measurement of the initial viscosity before immersion in water. The viscosity was recorded as a viscosity after immersion in water.

[Formability]

Each of the conformable dermal compositions of Examples and Comparative Examples was kneaded with bare hands, and the composition was formed into a predetermined shape for evaluating the formability based on the following three criteria: Excellent: excellent formability, Good: slightly poor formability, and Poor: poor formability.

[Releasability from Fingers and Stickiness]

Each of the dermal compositions of Examples and Comparative Examples was kneaded with bare hands, and the composition was formed into a predetermined shape for evaluating the releasability from fingers and the stickiness based on the following three criteria: Excellent: not sticky, Good: slightly sticky, and Poor: sticky.

[Shape Retention After Immersion in Water]

A circular specimen having a diameter of 30 mm and a thickness of 1.5 mm was sampled from each of the dermal compositions of Examples and Comparative Examples. The specimen was immersed in a physiological saline (0.9% NaCl solution) such that only one surface of the specimen was immersed in the saline for 2 hours, and surface water was wiped out. A weight of 465 g was then put on the specimen, and the specimen was left to stand for 15 sec. The weight was then removed, and the degree of deformation of the specimen was visually evaluated based on the following three criteria: Excellent: substantially not deformed, Good: slightly deformed, and Poor: greatly deformed.

[Viscosity Reduction Rate]

The viscosity of each conformable dermal composition after immersion in physiological saline was compared to that before the immersion, and the viscosity reduction rate was determined from Expression (1).

[Adhesive Residue]

A circular specimen having a diameter of 20 mm and a thickness of 1.5 mm was sampled from each of the dermal compositions of Examples and Comparative Examples. The specimen was spread on a commercially available face plate for ostomy and was attacked to the abdomen of a healthy subject. After three days, the specimen was detached together with the face plate, and adhesive residue on the abdomen was visually evaluated as follows:

Excellent: the adhesive was not visually observed on the skin;

Poor: the adhesive was visually observed on the skin.

Table 2 shows the formulations in Examples 1 to 7, Table 4 shows the formulations in Examples 8 to 15 (in Tables 2 and 4, the content of each component is expressed by wt %). The results of evaluation are shown in Tables 3 and 5 and FIGS. 1 and 2.

TABLE 2

| | Example 1 | Example 2 | Example 3 | Example 4 | Example 5 | Example 6 | Example 7 |
|---|---|---|---|---|---|---|---|
| Ethylene-(vinyl acetate) copolymer | 6.1 | 6.1 | 6.1 | 6.1 | 6.1 | 9.6 | 4.8 |
| Polyisobutylene | 65.7 | 66.6 | 66.6 | 66.6 | 66.7 | 65.6 | 67.7 |
| Polyether-modified silicone | 6.8 | 6.8 | 6.8 | 6.8 | 6.8 | 6.8 | 6.8 |
| Silylated silica | 6.8 | 6.8 | 6.8 | 6.8 | 6.8 | 4.1 | 6.8 |
| Sodium carboxymethyl cellulose | 13 | 13 | 13 | 13 | 13 | 13 | 13 |
| Ceramide 2 | — | 0.1 | — | — | — | 0.3 | 0.3 |
| Lipid composition A | 1 | — | 0.1 | — | — | — | — |
| Lipid composition B | — | — | — | 0.1 | — | — | — |
| Citric acid | 0.6 | 0.6 | 0.6 | 0.6 | 0.6 | 0.6 | 0.6 |

TABLE 3

| | Viscosity (mPa · s) | | Viscosity reduction rate (%) | Formability | Shape retention after immersion in water | Adhesive residue |
|---|---|---|---|---|---|---|
| | Before immersion in water | After immersion in water | | | | |
| Example 1 | 22,850,000 | 4,238,000 | 81.45 | Excellent | Excellent | Excellent |
| Example 2 | 27,130,000 | 3,011,000 | 88.9 | Excellent | Excellent | * |
| Example 3 | 21,110,000 | 3,032,000 | 85.64 | Excellent | Excellent | * |
| Example 4 | 20,900,000 | 4,576,000 | 78.11 | Excellent | Excellent | * |
| Example 5 | 29,760,000 | 3,654,000 | 87.72 | Excellent | Excellent | * |
| Example 6 | * | * | * | Excellent | * | Excellent |
| Example 7 | * | * | * | Excellent | * | Excellent |
| Comparative Example 1 | 73,500,000 | 29,570 | 99.96 | Good | Poor | Poor |
| Comparative Example 2 | 13,780,000 | 383,200 | 97.22 | Excellent | Good | * |

The mark * in the table indicates that the measurement was not carried out (the same applies the following tables).

TABLE 4

| | Example 8 | Example 9 | Example 10 | Example 11 | Example 12 | Example 13 | Example 14 | Example 15 |
|---|---|---|---|---|---|---|---|---|
| HSBR | 0.5 | 0.5 | 3.4 | 0.5 | 0.5 | 0.5 | 0.5 | — |
| Liquid paraffin | 0.2 | 0.2 | 1.4 | 0.2 | 0.2 | 0.2 | 0.2 | — |

TABLE 4-continued

|  | Example 8 | Example 9 | Example 10 | Example 11 | Example 12 | Example 13 | Example 14 | Example 15 |
|---|---|---|---|---|---|---|---|---|
| Ethylene-(vinyl acetate) copolymer | 5.5 | 5.5 | 4.8 | 15.7 | 5.5 | 5.5 | 5.5 | 6.1 |
| Polyisobutylene | 72.4 | 58.7 | 69 | 62.2 | 58.7 | 58.7 | 58.7 | 65.6 |
| Tackifier | — | 13.7 | — | — | 13.7 | 13.7 | 13.7 | — |
| Polyether-modified silicone | — | — | — | — | — | — | — | 6.8 |
| Silica | 6.8 | 6.8 | 6.8 | 6.8 | 6.8 | 6.8 | 6.8 | — |
| Silylated silica | — | — | — | — | — | — | — | 6.9 |
| Sodium carboxymethyl cellulose | 13 | 13 | 13 | 13 | 13 | 13 | 13 | 13 |
| Ceramide 2 | — | — | — | — | — | — | — | — |
| Lipid composition A | 1 | 1 | 1 | 1 | — | — | — | 1 |
| Lipid composition C | — | — | — | — | 1 | — | — | — |
| Lipid composition D | — | — | — | — | — | 1 | — | — |
| Lipid composition E | — | — | — | — | — | — | 1 | — |
| Citric acid | 0.6 | 0.6 | 0.6 | 0.6 | 0.6 | 0.6 | 0.6 | 0.6 |

TABLE 5

|  | Viscosity (mPa · s) | | Viscosity reduction rate (%) | Formability | Shape retention after immersion in water | Adhesive residue |
|---|---|---|---|---|---|---|
|  | Before immersion in water | After immersion in water | | | | |
| Example 8 | 43,870,000 | 8,116,000 | 82 | Excellent | Excellent | Excellent |
| Example 9 | 44,370,000 | 31,500,000 | 29 | Excellent | Excellent | Excellent |
| Example 10 | 54,020,000 | 23,160,000 | 57 | Good | Excellent | Excellent |
| Example 11 | 117,500,000 | 24,320,000 | 79 | Good | Excellent | Excellent |
| Example 12 | 35,820,000 | 2,811,000 | 92 | Excellent | Excellent | Excellent |
| Example 13 | 60,490,000 | 31,160,000 | 48 | Excellent | Excellent | Excellent |
| Example 14 | 46,890,000 | 10,210,000 | 78 | Excellent | Excellent | Excellent |
| Example 15 | 39,210,000 | 4,628,000 | 88 | Excellent | Excellent | Excellent |

As shown in Tables 3 and 5 and FIGS. 1 and 2, the conformable dermal compositions according to the embodiment each exhibit a low viscosity reduction rate after immersion in water, satisfactory shape retention, and no stickiness indicating good releasability from fingers. In contrast, Comparative Examples 1 and 2 each exhibit a significantly decreased viscosity after immersion in water and loss of its shape.

The results demonstrate that in the dermal compositions of Comparative Examples, for example, the compatibility between shape retention after the use and appropriate releasability from fingers is insufficient.

In contrast, in each Example, the reduction in viscosity after immersion in water is prevented, and the shape is well maintained. It is accordingly presumed to continuously fill in the gap between a face plate for ostomy and skin when the composition is applied to the skin of an ostomy patient and to hardly cause adhesive residue.

In particular, the dermal compositions in Examples 8 to 14 containing hydrogenated styrene-butadiene rubber show a tendency of the reduction in viscosity after immersion in water to be prevented.

As described above, the conformable dermal composition according to the embodiment shows good formability into a predetermined shape, even if it is handled with bare hands of an aged person, has good conformability to skin, and also maintains the shape even after the use, i.e., after the contact with water such as excretion, without loss of its shape.

When an ostomy appliance is used, the conformable dermal composition according to the embodiment is suitable for filling in the gap and irregularities of the skin around the stoma in use of an ostomy appliance, enhancing the adhesion of the appliance, and preventing leakage of excretion.

The conformable dermal composition according to the embodiment also can be suitably applied to a damaged site, such as a wound, or a site where a gap or irregularities are generated and are required to be sealed, such as a catheter or drain insertion site or connection site.

FIGS. 3 to 6 show photographs of the conformable dermal compositions of the embodiment and Comparative Examples evaluated for the shape retention after immersion in water. The weight of 465 g used in the evaluation of shape retention after immersion in water was determined by estimating the force that is applied with fingers when a conformable skin-protecting material for an ostomy appliance is detached after the use. The specimens of the conformable dermal compositions according to the embodiment were hardly deformed. In contrast, the specimen of the dermal composition of Comparative Example 1 was significantly deformed, and the specimen of the dermal composition of Comparative Example 2 was also deformed. If the shape retention after actual use is poor, an ostomy product including the dermal composition is presumed to show unsatisfactory impression from use in removal after the use and an insufficient aptitude for leakage of feces during the use. The conformable dermal compositions according to the embodiment are presumed to be suitable for filling in the gap and irregularities of the skin around a stoma in use of an ostomy appliance, enhancing the adhesion of the appliance, and preventing leakage of excretion.

The invention claimed is:

1. A conformable composition for skin application comprising:
   ethylene-(vinyl acetate) copolymer as a reinforcing component;

polyisobutylene and polyisoprene as a rubber adhesive component;
carboxymethyl-cellulose sodium and pectin as a hydrophilic polymer compound;
sphingolipids as a physiological activator;
alicyclic saturated hydrocarbon resin as a tackifier; and
the pectin as a pH adjusting agent,
wherein:
the wt % of the reinforcing component is 3 to 10, and
the wt % of the rubber adhesive component is 40 to 80.

2. The conformable composition for skin application according to claim 1, further comprising a surfactant.

3. The conformable composition for skin application according to claim 1, further comprising at least one selected from the group consisting of sterols, glycerol fatty acid esters, and higher alcohols.

4. The conformable composition for skin application according to claim 1, further comprising at least one selected from the group consisting of sterols, and surfactants and a higher alcohol.

5. The conformable composition for skin application according to claim 1, further comprising 0.3 to 30 wt % silica.

6. The conformable composition for skin application according to claim 5, wherein the silica is silylated silica.

7. The conformable composition for skin application according to claim 1, further comprising modified silicone.

8. The conformable composition for skin application according to claim 1, having a viscosity reduction rate defined by Expression (1) is 95% or less at 2 hours after immersion in water:

[Expression 1]

$$\text{Viscosity reduction rate (\%)} = \{1 - (\text{viscosity of sample after immersion in water})/(\text{viscosity of sample before immersion in water})\} \cdot 100 \quad (1).$$

9. The conformable composition for skin application according to claim 1,
wherein the conformable composition for skin application is applicable onto skin around a stoma and/or to an ostomy appliance with bare hands.

10. The conformable composition for skin application according to claim 1, wherein the wt % of the reinforcing component is 4.8 to 9.6.

11. The conformable composition for skin application according to claim 1, wherein the wt % of the rubber adhesive component is 58.7 to 72.4.

12. The conformable composition for skin application according to claim 10, wherein the wt % of the rubber adhesive component is 58.7 to 72.4.

* * * * *